(12) United States Patent
Wright

(10) Patent No.: US 6,206,828 B1
(45) Date of Patent: Mar. 27, 2001

(54) STERNAL RETRACTOR WITH CHANGEABLE BLADES AND BLADE LATCH MECHANISM

(76) Inventor: John T. M. Wright, 555 S. Downing St., Denver, CO (US) 80209

( * ) Notice: Subject to any disclaimer, the term of this patent is extended or adjusted under 35 U.S.C. 154(b) by 0 days.

(21) Appl. No.: 09/327,634

(22) Filed: Jun. 8, 1999

(51) Int. Cl.[7] ................................................. A61B 17/02
(52) U.S. Cl. ............................................. 600/232; 600/233
(58) Field of Search .................................. 600/231, 232, 600/233

(56) References Cited

U.S. PATENT DOCUMENTS

| | | | |
|---|---|---|---|
| 3,965,890 | * | 6/1976 | Gauthier ................................ 600/232 |
| 4,865,019 | * | 9/1989 | Phillips .................................. 600/232 |
| 5,772,583 | * | 6/1998 | Wright et al. ......................... 600/232 |
| 5,795,291 | * | 8/1998 | Koros et al. .......................... 600/232 |
| 5,846,193 | * | 12/1998 | Wright ................................... 600/232 |
| 5,984,867 | * | 11/1999 | Deckman et al. .................... 600/232 |
| 5,993,385 | * | 11/1999 | Johnston et al. ..................... 600/232 |

* cited by examiner

Primary Examiner—Paul J. Hirsch

(57) ABSTRACT

A surgical retractor with a special latch mechanism and arrangement for changing retractor blades without tools during surgery is disclosed.

12 Claims, 3 Drawing Sheets

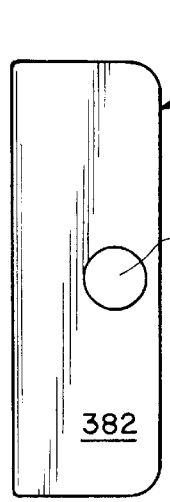
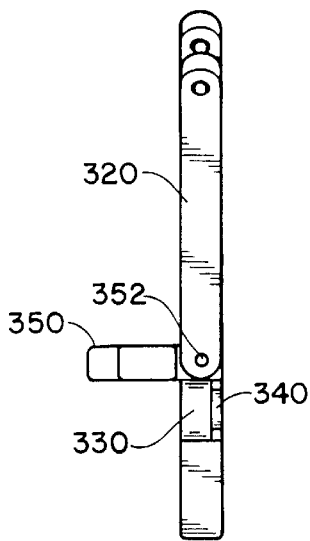
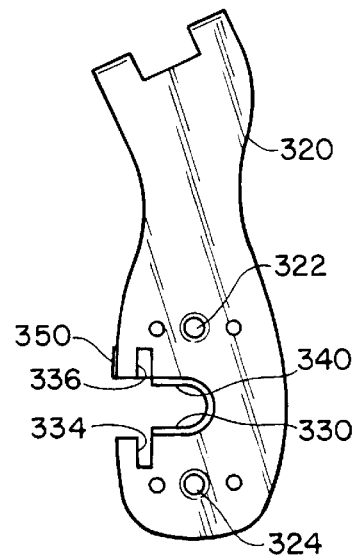
FIG. 8   FIG. 9   FIG. 10
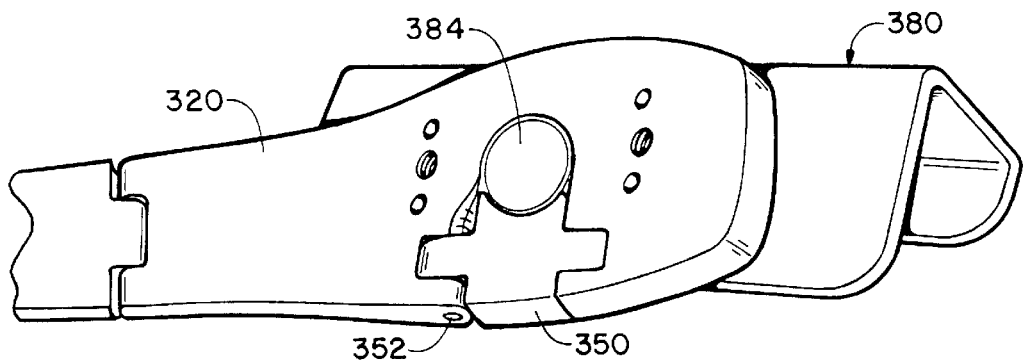
FIG. 11
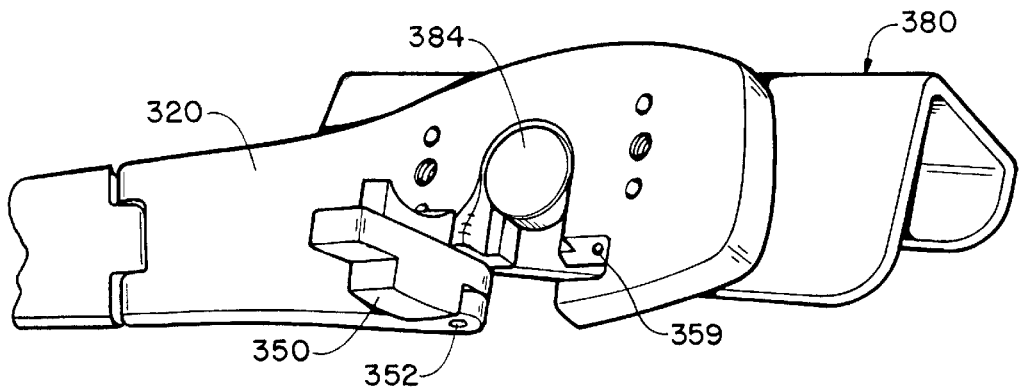
FIG. 12

STERNAL RETRACTOR WITH CHANGEABLE BLADES AND BLADE LATCH MECHANISM

FIELD OF THE INVENTION

This invention relates to an improved sternal retractor for use in open heart surgery. More specifically, this invention relates to an improvement in sternal retractors that comprise, in use, a pair of oppositely open facing retractor blades.

The present invention is especially advantageous for use in child and pediatric surgery. The invention may also be used in adult coronary artery bypass surgery and valve repair or replacement surgery.

BACKGROUND OF THE INVENTION

Surgery of the heart is a common surgical procedure and about 600,000 are currently performed in the worldwide each year, of which about half take place in the U.S. Most heart operations involve coronary artery bypass grafting, but a significant number involve heart valve replacement or repair, including replacement or valvuloplasty of mitral and tricuspid valves. This surgical technique requires adequate exposure of the valve annulus. Good exposure of the mitral valve is a difficult problem in some patients due to individual anatomy. The heart is usually exposed by a sternal midline incision. Following the opening of the sternum a sternal retractor is used to open the sternum a distance of several inches.

In general, the typical retractor consists of two sternal blades attached, respectively, to a pair of arms. One arm is rigidly attached to a rack containing a single row of gear teeth, and the second arm rigidly fixed to a moving member that is able to slide along the rack. A rotatable handle, hinged to a simple cog gear is contained in the moving member and engages the rack. Rotation of the handle caused the member to move along the rack, thus changing the separation distance between the sternal blades.

While surgical retractors, in general, perform the same function—spreading apart two adjacent anatomical structures to permit access by the surgeon— the requirements for a satisfactory retractor for one purpose differ greatly from requirements for a retractor intended for a different surgical procedure. Thus, there is no basis for extrapolating a function, structure or concept from one kind of retractor to another kind of retractor. A rib cage retractor, or a back retractor, for example, teaches little of any value or relevance with respect to a sternal retractor or a jaw retractor.

An example of a sternal retractor of the general type of which the present invention is an improvement is described in U.S. Pat. No. 5,772,583, Wright, et. al., The Wright, et. al., patent also describes and refers to several other retractors that constitute prior art as to the present invention.

It is important in some surgical procedures to be able to position the retractor operating mechanism without retractor blades attached and/or to be able to use any of a plurality of blades of different sizes and shapes—being able to interchange blades as need during surgery. This result has not been reasonably possible using prior art retractors. Indeed, the general approach has been to select a given retractor and then to modify surgical procedures as necessary to accommodate the selected retractor.

SUMMARY OF THE INVENTION

This invention offers a clear advantage by providing a surgical instrument design that conforms to conform the surgical protocol and to the surgeon's needs—rather than requiring the surgeon to work around the limitations of the surgical instrument.

The present invention incorporates advantages from my previous patent, U.S. Pat. No. 5,772,583, Wright, et. al., wherein trauma caused by opening the chest, which may be opened along a curved path that lies close to the patient's body is reduced. The retractor blades are free to pivot, typically about 10° in either direction, to automatically align with the cut edges of the sternum to spread the pressure evenly over the length of the blades.

It is of particular importance in pediatric surgery that retractor blades of exactly the correct length be used to minimize patient trauma. In the past, several retractors of different sizes were required to be on hand because the blades could not in any reasonable way be interchanged. One of the features of this invention is the provision of a retractor with changeable blades.

The force of the retractor is, of course, exerted through the retractor blade to the patient. Thus, the blade must be so attached to the retractor actuating mechanism as to withstand the forces applied thereto during surgery. A new and uniquely simple and certain locking mechanism is provided that permits the surgeon, or an assistant, to exchange blades on the retractor at the operating table.

BRIEF DESCRIPTION OF THE DRAWINGS

FIG. 4 is a bottom plan view of top plan view of a first of the two hinged arms that are part of the invention, the top plan view being shown in FIG. 3.

FIG. 8 is a top view of an alternative form of the removable blade, the pivot limiting pin being omitted.

FIGS. 9 and 10 are, respectively, side and bottom views of another or second pivotal arm of the invention.

FIGS. 11 and 12 are perspective views of the hinged arm of the invention taken from the top on the distal side of the blade, wherein:

FIG. 11 shows the blade locked into position.

FIG. 12 shows the blade in position but not locked and, therefore, ready to be removed from attachment to the arm.

DESCRIPTION OF THE PREFERRED EMBODIMENTS

The drawings are merely exemplary, intended to teach the manner of making and using the invention and are not limiting. Materials and specific shapes of components are not critical—it is required only that the components be compatible in size and shape to allow the functions described to be accomplished. Many alternative embodiments of the invention are available to the user and to engineers without departing from the scope of the invention.

The present invention is an improvement over prior art devices in use and shown in the literature and, thus, some components of this invention are functionally the same and may be structurally quite similar to certain prior art devices. In this regard, the present invention is an improvement over applicant's invention described in U.S. Pat. No. 5,772,583, the disclosure of which is incorporated herein by reference.

Figure 1:
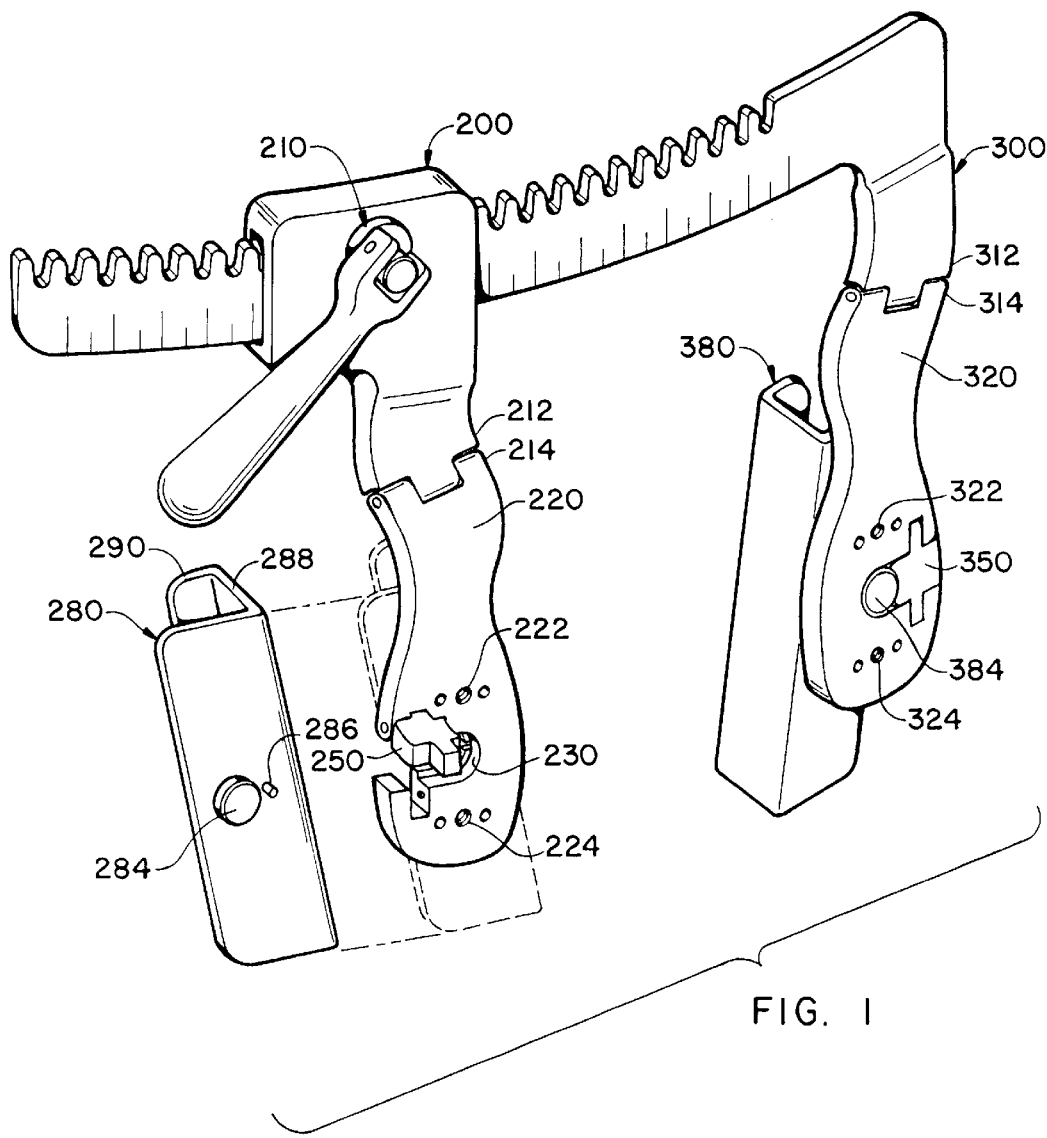
FIG. 1 is a perspective, partially exploded view, of the side of the retractor of this invention that is exposed in use. Since this side of the retractor normally faces upwardly, FIG. 1 may properly be described as a top view, in partial perspective, partial exploded view of the invention.
Figure 2:
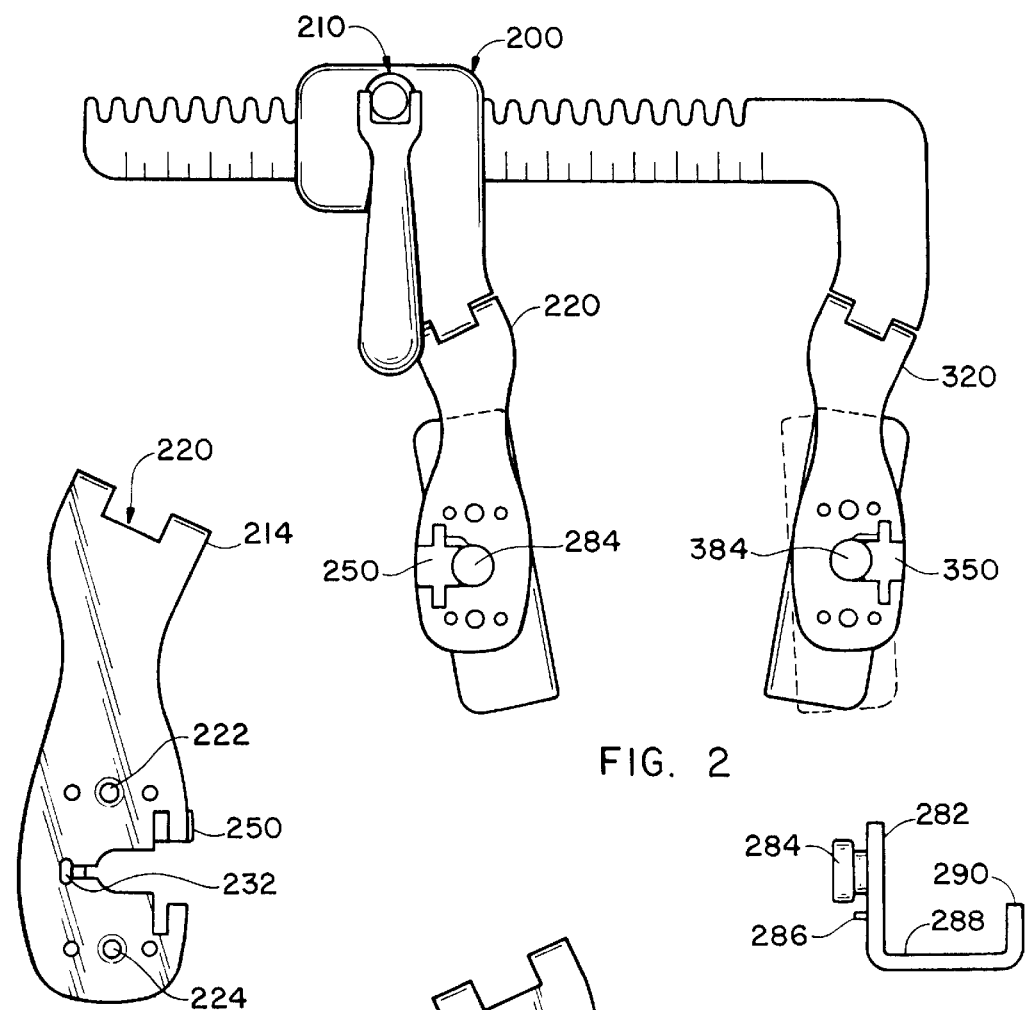
FIG. 2 is a top plan view of the invention, showing in dashed lines the blade in a different position than that shown in solid line.

Referring to the drawings, to FIG. 1 in particular, the rack 100, moveable arm 200 with its pinion 210 and the fixed arm 300 may be functionally the same as and structurally similar to corresponding structure in said U.S. Pat. No. 5,772,583. Said patent also discloses, on each of the arms, a hinged arm to which the retractor blades are attached—permanently in the case of said patent. Thus, in a general sense the hinged arm 220, connected by hinge components 212 and 214, to arm 200 and the hinged arm 320, connected by hinge components 312 and 314 to arm 300 correspond to the hinged arms disclosed in said U.S. Pat. No. 5,772,583.

The sternal retractor has pivoting sternal blades that are free to rotate up to at least about ten degrees which allow a more natural opening of the chest, which should significantly reduced the incidence of complications due to sternal fracture. The rack of the retractor, in a preferred embodiment, has a downward curve appropriate to correspond to the curvature of the chest of the patient. Such curvature is not necessary to the invention, however. The arms of the retractor have inclined hinges. The curved rack of the sternal retractor, combined with the hinged arms, allows more natural opening of the chest whilst not obstructing the surgeon work area. A measuring scale on the rack helps prevent over extension of the sternum.

Except for the attachment of the blades to the hinged arms, and removal of the blades from attachment to the hinged arms, which is described hereinafter, the method of using the retractor during surgery is the same as the method of using the prior art retractors. The medical literature is replete with disclosures of how retractors may be used and the skilled surgeon is intimately familiar with how these devices are used.

Referring again to the drawings, FIGS. 1 through 7 in particular, the structure of the improvement in hinged arm and locking mechanisms are described. The hinged arm 220 typically has sets of attachment guide apertures 222 and 224 which are used to attach other devices during surgery. Typically, the center of the three holes shown is threaded to permit screw attachment of devices to the arm and the other of the two holes are simply guide holes to receive pins. Such arrangements for permitting attachment of other devices are common and well-known to those skilled in the art.

Figure 4:
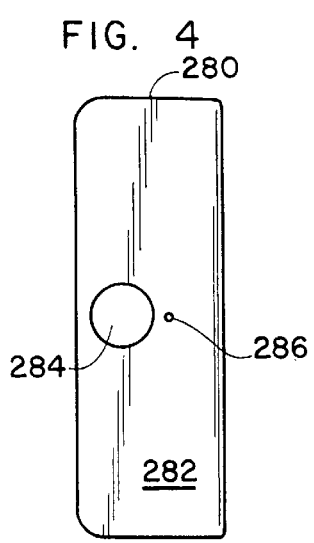
FIGS. 3 and 4 are, respectively, a top plan view and a bottom plan view of a first of the two hinged arms that are part of the invention, the latch being shown in the open position.
Figure 3:
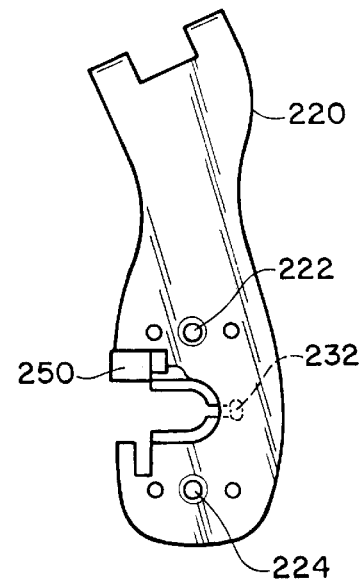
Figure 6:
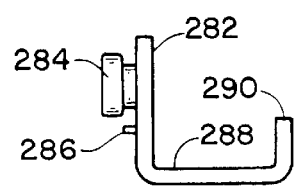
FIGS. 5, 6 and 7 are, respectively, top, end and side views of one form of the removable blade that is attachable to the respective hinged arms.
Figures 5, 7:
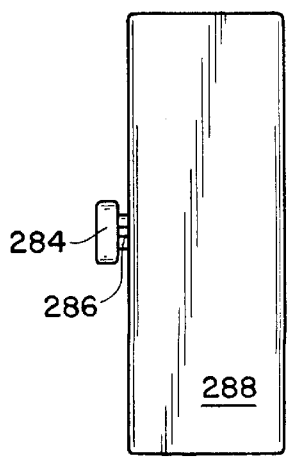

An elongate slot 230 is formed in the hinged arm on the distal edge of the arm. The slot terminates in an arc extending through the thickness of the arm. In the preferred embodiment, side slots 234 and 236 extend from and perpendicular to the slot 230. As best shown in FIGS. 3 and 4, a recess 232 is configured and constructed to extend through only about one-third to one-half the thickness of the arm 220 beyond the end of the slot 230, toward the proximal edge of the arm. The slot 232 is formed in the bottom or distal side of the arm, as shown in dashed lines in FIG. 3 and as indicated in FIG. 4. As best shown in FIG. 3, the arm is configured and constructed to define a generally arcuate recess 240 extending outwardly around a substantial portion of the internal end of the slot 230. The arcuate recess extends from the outer or proximal side of the arm 220 about one-third to two-thirds the thickness of the arm. The arcuate recess is, as shown in FIG. 3, on the opposite side of the arm 220 from the slot 232. The combined structure of the slot 230 and the arcuate recess 240 is configured and formed in the arm 220 so as to define a slot extending from an edge of the arm toward the other edge of the arm terminating in an arcuate flanged passage through the arm for receiving and retaining perpendicularly to the plane of the arm a pivot pin 284 described hereinafter.

Referring now to FIGS. 1 through 7 again, attention is invited to the retractor blade 280. It will be seen that the retractor blade is in all essential respects similar to prior art retractor blades, except for the structure permitting removal from and attachment with the arms. The blade 280 comprises a proximal, or upper, surface 282 from which extends a strong post of generally T-shaped cross-section, i.e., having a shaft extending from the surface with an enlarged head. The head is substantially circular having a diameter substantially the larger than the arc of slot 230 and the same as or slightly less than the diameter of the arcuate recess 240. In addition, the blade may comprise a pivot limiting pin 286 receivable in the recess 232 when the blade is secured to the retractor. The blade also comprises, in common with many prior art blades, a downward extending back portion 288 and a proximal extending blade portion 290.

Referring now to the drawings, and particularly to FIGS. 11 and 12, a locking latch 350 is pivotally secured at one end thereof by a pivot pin or structure 352 in the slot 336 and can pivot from a closed and latched position as shown in FIG. 11 to and open position as shown in FIG. 12. The latch is maintained in the latched position by any suitable retainer, such as a ball detent mechanism indicated at 354.

Reference is made now to FIGS. 8 through 12 wherein the other or second hinged arm and blade combination are depicted. In general, while the overall peripheral configuration of the hinged arm 320 differs from the hinged arm 220, the configuration and construction is the same. Likewise, the blade 380 is generally the same as, and may be identical to, the blade 280. Simply to illustrate one simple choice one may make, however, the blade 380 does not include a pivot limiting pin corresponding to pin 286. The post 384 would, in most instances, be identical to the post 284 as to structure and size.

The structural components of the arm 320 correspond to the structural components of the arm 220, comprising the slot 330 and recess 340, the side-slots 332 and 334 and the latch 350 corresponding structures 230, 232, 234, 240 and 250 in arm 220. In common with the arm 220, but not shown in the previous figures, the latch 350 is pivotally secured by a pin or other means in the slot 232 for pivoting between and open position, shown in FIG. 12, to a closed or latched position, shown in FIG. 11, being locked in the latched position by suitable means such as a ball-detent mechanism 354 shown in FIG. 12. As indicated corresponding structure is found in both arms 220 and 320. The arm 320 may or may not include a groove corresponding to recess 232, at the option of the maker or user. In the preferred embodiment, the latch is so constructed and configured as to define an arcuate portion 356 for direct engagement with the pin 384.

The method of using this invention will now be apparent. Reference is made to FIGS. 11 and 12 in the following discussion. When, during surgery, it is determined that a shorter or longer, or a wider or deeper retraction blade would facilitate the surgical procedure, the surgeon merely loosens the retractor slightly, opens the latch 350, moving it from the position shown in FIG. 11 to the position shown in FIG. 12 and removes the blade by sliding it out of the groove 330—toward the bottom of the page as shown on the drawing. The new selected blade is slid into the groove 330 to the end thereof and the latch 350 is moved from the open position, shown in FIG. 12, to the closed position, shown in FIG. 11, and the latch locked into place by the ball detent 354.

The foregoing blade change can be accomplished without hand tools and without removal of the retractor from the operating field. The replacement can be accomplished in less than a minute, this minimizing time on the operating table and the resulting trauma. Only one retractor need be provided, along with a set of retractor blades of different sizes.

The retractor may be made of any strong material compatible with surgery. Stainless steel, various cobalt alloys, and titanium and its alloys, for example, may be used.

It will be understood that the specific components may take on any of many configurations and that the invention is limited only by the scope of the claims appended hereto.

INDUSTRIAL APPLICATION

This invention is useful in the medical and surgical instrument industries.

What is claimed is:

1. A method of carrying out surgery by spreading the patients tissue or bone structures apart using a rack and pinion retractor that comprises a pair of opposed retractor blades carried by a pair of arms to gain access to the organs inside the chest, the retractor being configured and constructed to permit the respective arms to be moved reciprocally toward and away from each other by the rack and pinion, the improvement comprising positioning in a surgical incision in the patient a rack and pinion retractor wherein at least one of the opposed blades is removably retained on the respective arms by latch means pivotally attached to the respective arms capable of being moved by the surgeon without tools from a closed position retaining the blade on the arm to an open position to permit the blade to be removed by the surgeon without tools from the arm, and replacing during surgery one blade with a different blade.

2. In a retractor comprising a rack and pinion, first and second arms attached to the rack and pinion movable by the rack and pinion toward and away from each other, hinged first and second arms hingably connected respectively to the first and second arms attached to the rack and pinion, first and second retractor blades pivotally attached to the respective hinged arms for engaging and spreading of the sternum of a patient during surgery, the improvement wherein at least one of the respective blades is removably attached to the respective arm by means pivotally attached to the respective arms for selectively latching the blade to the arm and unlatching the blade to permit the blade to be removed from the arm and a different blade to be attached to the blade all without the use of tools.

3. In a retractor comprising a rack and pinion, first and second arms attached to the rack and pinion movable by the rack and pinion toward and away from each other, hinged first and second arms hingably connected respectively to the first and second arms attached to the rack and pinion, first and second retractor blades pivotally attached to the respective hinged arms for engaging and spreading of the sternum of a patient during surgery, the improvement further comprising latch means pivotally attached to at least one of the arms for removably latching one of the blades to said arm for being attached to and removed from attachment with the blade during surgery without the use of tools.

4. The retractor of claim 3 wherein the latch means comprises a slot in the arm and a latch pivotally mounted to open or close the slot to entry of the blade.

5. The retractor of claim 4 wherein the latch means comprises a means for retaining the latch in the position thereof closing the slot to entry of the blade.

6. The retractor of claim 5 wherein the means for retaining the latch in the position thereof closing the slot to entry of the blade is a detent mechanism.

7. The retractor of claim 3 wherein at least one of the respective retractor blade comprises a post having a T-shaped cross-section comprising a head portion and shaft portion, and wherein the post is so configured and constructed to be slidable without the use of tools into and out from the slot, the post being pivotal in the slot when the latch means closes the slot.

8. The retractor of claim 7 wherein at least one of the respective retractor blades and at least one of the respective arms comprise structures configured and constructed to limit pivotal movement of the blade in the slot, with the latch closed, to about ten degrees.

9. The retractor of claim 7 wherein each of the respective retractor blades comprises a post having a T-shaped cross-section comprising a head portion and shaft portion, and wherein the post is so configured and constructed to be slidable without the use of tools into and out from the slot in the respective arms, the post being pivotal in the slot when the latch means closes the slot.

10. The retractor of claim 9 wherein the latch means comprises a slot in the arm and a latch pivotally mounted to open or close the slot to entry of the blade.

11. The retractor of claim 10 wherein the latch means comprises a means for retaining the latch in the position thereof closing the slot to entry of the blade.

12. The retractor of claim 11 wherein the means for retaining the latch in the position thereof closing the slot to entry of the blade is a detent mechanism.

* * * * *